United States Patent    (10) Patent No.: US 10,712,416 B1
Sandino et al.                (45) Date of Patent:      Jul. 14, 2020

(54) METHODS AND SYSTEMS FOR MAGNETIC RESONANCE IMAGE RECONSTRUCTION USING AN EXTENDED SENSITIVITY MODEL AND A DEEP NEURAL NETWORK

(71) Applicants: GE Precision Healthcare, LLC, Milwaukee, WI (US); The Board of Trustees of the Leland Stanford Junior University, Stanford, CA (US)

(72) Inventors: Christopher Michael Sandino, Menlo Park, CA (US); Peng Lai, Union City, CA (US); Shreyas Vasanawala, Stanford, CA (US); Joseph Yitan Cheng, Los Altos, CA (US)

(73) Assignees: GE PRECISION HEALTHCARE, LLC, Milwaukee, WI (US); THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

(21) Appl. No.: 16/268,201

(22) Filed: Feb. 5, 2019

(51) Int. Cl.
*G01R 33/56* (2006.01)
*G01R 33/58* (2006.01)
(Continued)

(52) U.S. Cl.
CPC ......... *G01R 33/5608* (2013.01); *G01R 33/58* (2013.01); *G06N 3/08* (2013.01);
(Continued)

(58) Field of Classification Search
CPC ...... G01R 33/5608; G01R 33/58; G06N 3/08; G16H 30/40; G06T 11/005; G06T 11/008; G06T 2211/424
See application file for complete search history.

(56) References Cited

U.S. PATENT DOCUMENTS 6,841,998 B1   1/2005 Griswold
8,379,951 B2   2/2013 Lustig et al.
(Continued)

OTHER PUBLICATIONS

Pruessmann, K. et al., "SENSE: Sensitivity Encoding for Fast MRI," Magnetic Resonance in Medicine, vol. 42, No. 5, Nov. 1999, Available Online Oct. 28, 1999, 11 pages.
(Continued)

*Primary Examiner* — G. M. A Hyder
(74) *Attorney, Agent, or Firm* — McCoy Russell LLP

(57) ABSTRACT

Various methods and systems are provided for reconstructing magnetic resonance images from accelerated magnetic resonance imaging (MRI) data. In one embodiment, a method for reconstructing a magnetic resonance (MR) image includes: estimating multiple sets of coil sensitivity maps from undersampled k-space data, the undersampled k-space data acquired by a multi-coil radio frequency (RF) receiver array; reconstructing multiple initial images using the undersampled k-space data and the estimated multiple sets of coil sensitivity maps; iteratively reconstructing, with a trained deep neural network, multiple images by using the initial images and the multiple sets of coil sensitivity maps to generate multiple final images, each of the multiple images corresponding to a different set of the multiple sets of sensitivity maps; and combining the multiple final images output from the trained deep neural network to generate the MR image.

18 Claims, 8 Drawing Sheets

(51) Int. Cl.
*G16H 30/40* (2018.01)
*G06T 11/00* (2006.01)
*G06N 3/08* (2006.01)

(52) U.S. Cl.
CPC .......... *G06T 11/005* (2013.01); *G06T 11/008* (2013.01); *G16H 30/40* (2018.01); *G06T 2211/424* (2013.01)

(56) References Cited

U.S. PATENT DOCUMENTS

2017/0146627 A1* 5/2017 Cheng .............. G01R 33/56316
2017/0309019 A1 10/2017 Knoll et al.
2018/0285695 A1* 10/2018 Guo ........................ A61B 5/055
2019/0236817 A1* 8/2019 Cheng ................ G01R 33/5608

OTHER PUBLICATIONS

Griswold, M. et al., "Generalized Autocalibrating Partially Parallel Acquisitions (GRAPPA)," Magnetic Resonance in Medicine, vol. 47, No. 6, Jun. 7, 2002, 9 pages.
Daubechies, I. et al., "An Iterative Thresholding Algorithm for Linear Inverse Problems with a Sparsity Constraint," Communications on Pure and Applied Mathematics, vol. 57, No. 11, Nov. 2004, Available Online Aug. 26, 2004, 45 pages.
Griswold, M. et al., "Field-of-View Limitations in Parallel Imaging," Magnetic Resonance in Medicine, vol. 52, No. 5, Nov. 2004, Available Online Oct. 26, 2004, 9 pages.
Block, K. et al., "Undersampled Radial MRI with Multiple Coils. Iterative Image Reconstruction Using a Total Variation Constraint," Magnetic Resonance in Medicine, vol. 57, No. 6, Jun. 2007, Available Online May 29, 2007, 13 pages.
Lustig, M. et al., "Sparse MRI: The Application of Compressed Sensing for Rapid MR Imaging," Magnetic Resonance in Medicine, vol. 58, No. 6, Dec. 2007, Available Online Oct. 29, 2007, 14 pages.
Lustig, M. et al., "SPIRiT: Iterative Self-consistent Parallel Imaging Reconstruction From Arbitrary k-Space," Magnetic Resonance in Medicine, vol. 64, No. 2, Aug. 2010, Available Online Jul. 20, 2010, 15 pages.
Uecker, M. et al., "ESPIRiT—An Eigenvalue Approach to Autocalibrating Parallel MRI: Where SENSE meets GRAPPA," Magnetic Resonance in Medicine, vol. 71, No. 3, Mar. 2014, Available Online May 6, 2013, 28 pages.
Parikh, N. et al., "Proximal Algorithms," Foundations and Trends in Optimization, vol. 1, No. 3, Jan. 13, 2014, 113 pages.
He, K. et al., "Deep Residual Learning for Image Recognition," Proceedings of the 2016 IEEE Conference on Computer Vision and Pattern Recognition (CVPR), Jun. 27, 2016, Las Vegas, Nevada, 9 pages.
Zhang, T. et al., "Robust Self-navigated Body MRI Using Dense Coil Arrays," Magnetic Resonance in Medicine, vol. 76, No. 1, Jul. 2016, Available Online Jul. 29, 2015, 16 pages.
Virtue, P. et al., "Better Than Real: Complex-Valued Neural Nets for MRI Fingerprinting," Proceedings of the 2017 IEEE International Conference on Image Processing (ICIP), Sep. 17, 2017, Beijing, China, 5 pages.
Schlemper, J. et al., "A Deep Cascade of Convolutional Neural Networks for Dynamic MR Image Reconstruction," IEEE Transactions on Medical Imaging, vol. 37. No. 2, Feb. 2018, Available Online Oct. 13, 2017, 14 pages.
Cheng, J. et al., "Highly Scalable Image Reconstruction using Deep Neural Networks with Bandpass Filtering," arXiv Website, Available Online at https://arxiv.org/pdf/1805.03300.pdf, May 8, 2018, 9 pages.
Hammernik, K. et al., "Learning a Variational Network for Reconstruction of Accelerated MRI Data," Magnetic Resonance in Medicine, vol. 79, No. 6, Jun. 2018, Available Online Nov. 8, 2017, 29 pages.
Diamond, S. et al., "Unrolled Optimization with Deep Priors," arXiv Website, Available Online at https://arxiv.org/pdf/1705.08041.pdfm, Dec. 20, 2018, 11 pages.
Qin, C. et al., "Convolutional Recurrent Neural Networks for Dynamic MR Image Reconstruction," IEEE Transactions on Medical Imaging, vol. 38, No. 1, Jan. 2019, Available Online Aug. 6, 2018, 11 pages.

\* cited by examiner

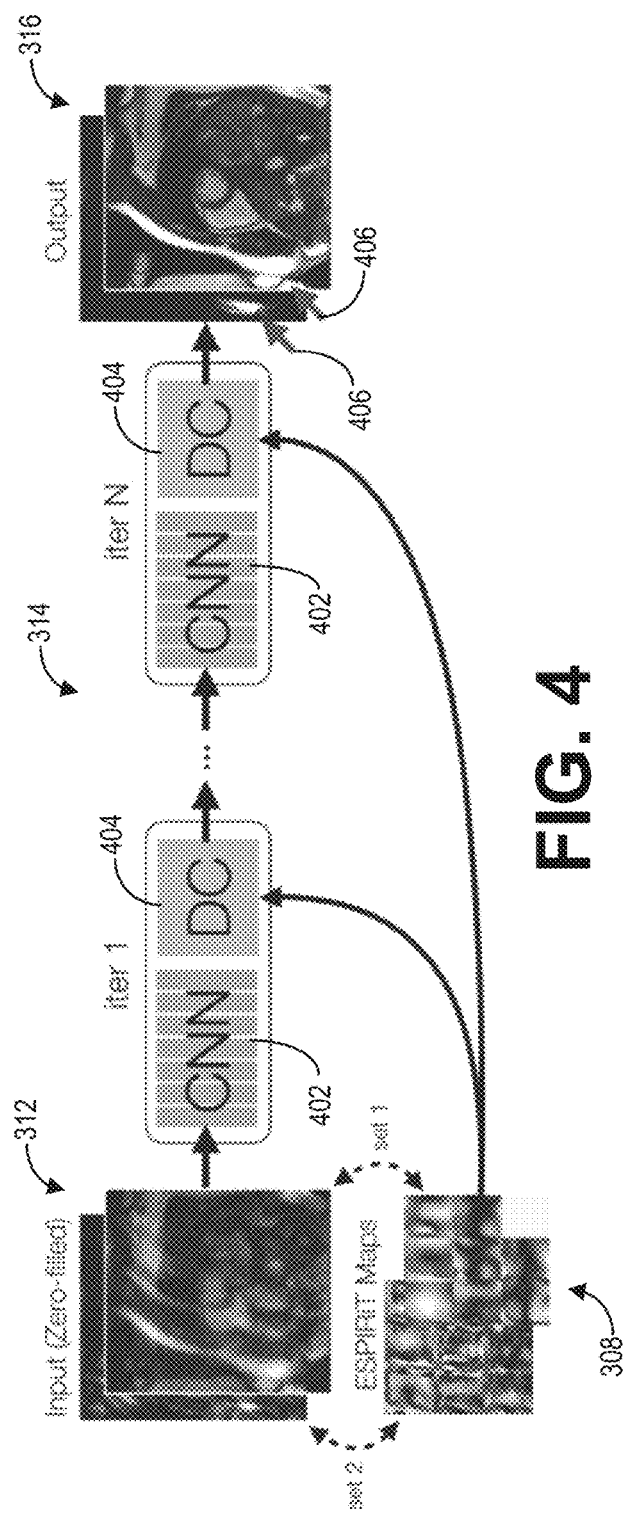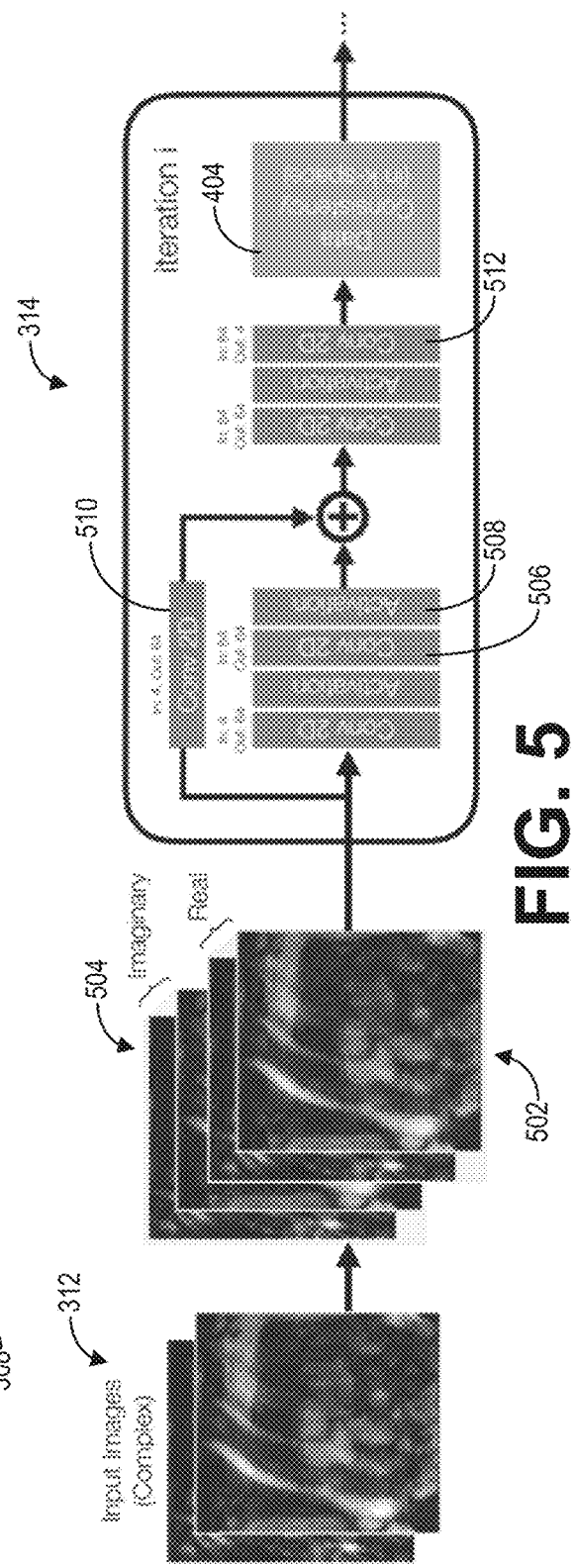
FIG. 4
FIG. 5

_US 10,712,416 B1_

METHODS AND SYSTEMS FOR MAGNETIC RESONANCE IMAGE RECONSTRUCTION USING AN EXTENDED SENSITIVITY MODEL AND A DEEP NEURAL NETWORK

ACKNOWLEDGEMENT OF GOVERNMENT SUPPORT

This invention was made with government support under contract no. EB009690 awarded by the National Institutes of Health. The government has certain rights in the invention.

FIELD

Embodiments of the subject matter disclosed herein relate to magnetic resonance imaging, and more particularly, to deep learning-based magnetic resonance image reconstruction with an extended coil sensitivity model.

BACKGROUND

Magnetic resonance imaging (MRI) is a medical imaging modality that can create images of the inside of a human body without using x-rays or other ionizing radiation. MRI uses a powerful magnet to create a strong, uniform, static magnetic field. When the human body, or part of the human body, is placed in the magnetic field, the nuclear spins associated with the hydrogen nuclei in tissue water become polarized, wherein the magnetic moments associated with these spins become preferentially aligned along the direction of the magnetic field, resulting in a small net tissue magnetization along that axis. MRI systems also include gradient coils that produce smaller amplitude, spatially-varying magnetic fields with orthogonal axes to spatially encode the magnetic resonance (MR) signal by creating a signature resonance frequency at each location in the body. The hydrogen nuclei are excited by a radio frequency signal at or near the resonance frequency of the hydrogen nuclei, which add energy to the nuclear spin system. As the nuclear spins relax back to their rest energy state, they release the absorbed energy in the form of an RF signal. This RF signal (or MR signal) is detected by one or more RF coil arrays and is transformed into the image using a computer and known reconstruction algorithms.

The MRI acquisition process may be slow due to the large volume of data collected. Undersampling, or collecting less k-space data, may decrease scan times; however, this may result in aliasing artifacts that may obscure relevant anatomy. Advanced MRI reconstruction techniques, such as parallel processing, may accelerate scan times by reducing the amount of data collection without aliasing.

BRIEF DESCRIPTION

In one embodiment, a method for reconstructing a magnetic resonance (MR) image include estimating multiple sets of coil sensitivity maps from undersampled k-space data, wherein the undersampled k-space data was acquired by a multi-coil radio frequency (RF) receiver array; reconstructing multiple initial images using the undersampled k-space data and the estimated multiple sets of coil sensitivity maps, each of the multiple initial images corresponding to a different set of the multiple sets of coil sensitivity maps; iteratively reconstructing, with a trained deep neural network, multiple images by using the initial images and the multiple sets of coil sensitivity maps to generate multiple final images, each of the multiple images corresponding to a different set of the multiple sets of sensitivity maps; and combining the multiple final images output from the trained deep neural network to generate the MR image. In this way, imaging artifacts may be reduced in a reconstructed image while also reducing computational effort of the reconstruction and scan times.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIG. 4 shows a schematic diagram of the deep learning-ESPIRiT network which can be used in FIG. 3, according to an exemplary embodiment.

FIG. 5 shows a layout of the deep learning-ESPIRiT network, according to an exemplary embodiment.

DETAILED DESCRIPTION

Magnetic resonance imaging (MRI) is a flexible diagnostic tool that enables non-invasive visualization of soft-tissue anatomy and physiology. However, the MRI acquisition process is inherently slow, limiting its clinical application in certain cases. Scan times during an MRI scan may be reduced by undersampling, or collecting less k-space data. However, undersampling may result in aliasing artifacts that may obscure relevant anatomy. Advanced MR image reconstruction techniques such as parallel imaging can dramatically accelerate scan times by reducing the amount of data collection needed to reconstruct MR images without aliasing. SENSE (sensitivity encoding) utilizes explicit knowledge of coil array sensitivities to spatially localize signals and de-alias undersampled images. GRAPPA (generalized autocalibrating partial parallel acquisition) exploits local correlations across coils in k-space to synthesize missing data samples.

Each of these approaches have tradeoffs and another approach, termed ESPIRiT, combines SENSE and GRAPPA to inherit benefits from both techniques. ESPIRiT uses a flexible coil sensitivity model, which can incorporate non-Cartesian sampling trajectories and arbitrary image priors. ESPIRiT is robust to artifacts that arise from inconsistent coil sensitivity maps by using an extended coil sensitivity model which employs multiple sets of coil sensitivity maps. For example, objects that are larger than the prescribed field of view (FOV) can overlap and create discontinuities in sensitivity maps resulting in ghosting along the phase encoding direction. However, ESPIRiT is able to represent overlapping anatomies with multiple sets of coil sensitivity maps (as compared to only a single set of coil sensitivity maps), allowing overlapping components to be de-aliased separately from each other. Details of the ESPIRiT approach were described in "ESPIRiT—An eigenvalue approach to autocalibrating parallel MRI: Where SENSE meets GRAPPA," M. Uecker et al., *Magnetic Resonance in Medicine*, vol. 71, no. 3, pp. 990-1001, 2014.

Figure 8:
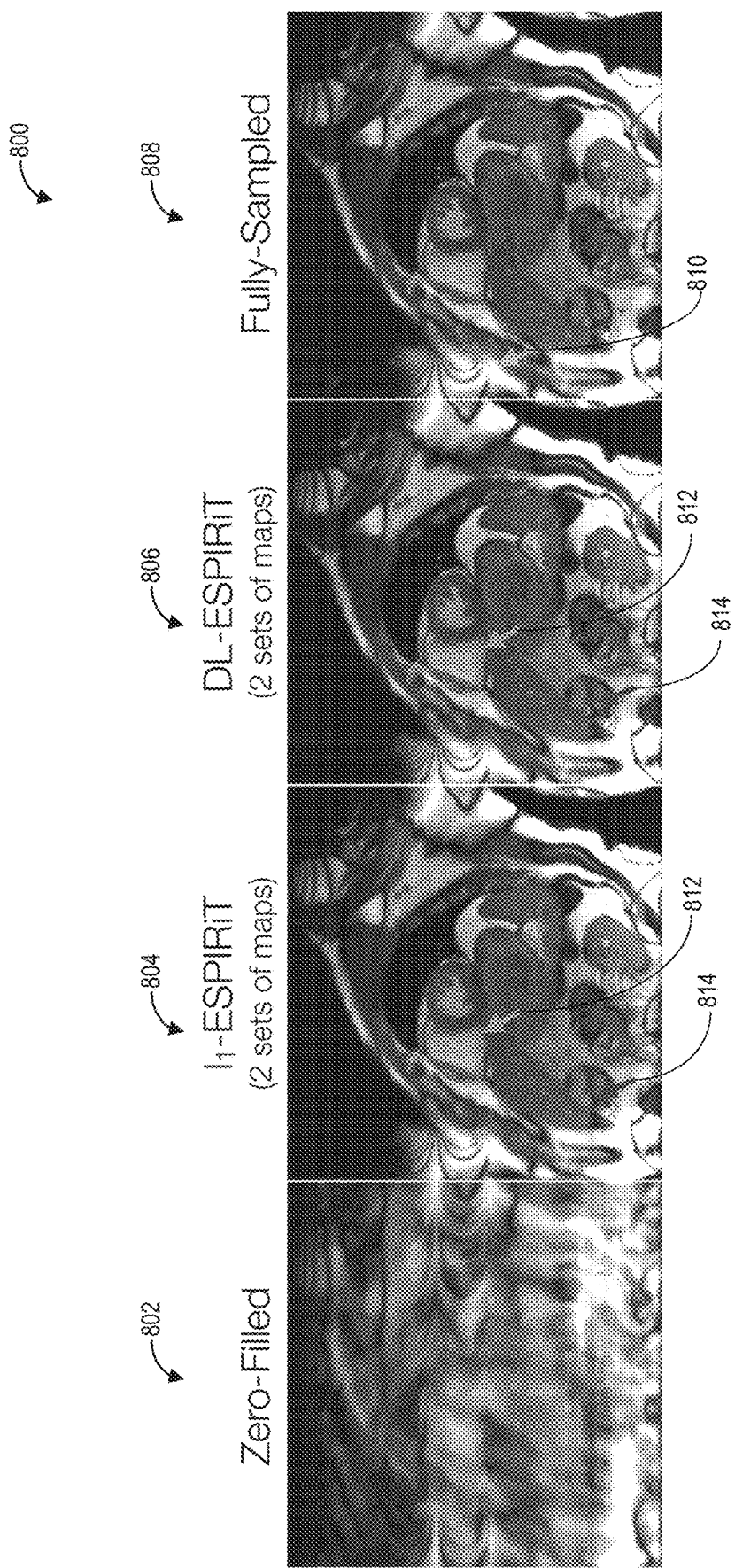
FIG. 8 shows a first set of cardiac MR images reconstructed by different techniques.
Figure 9:
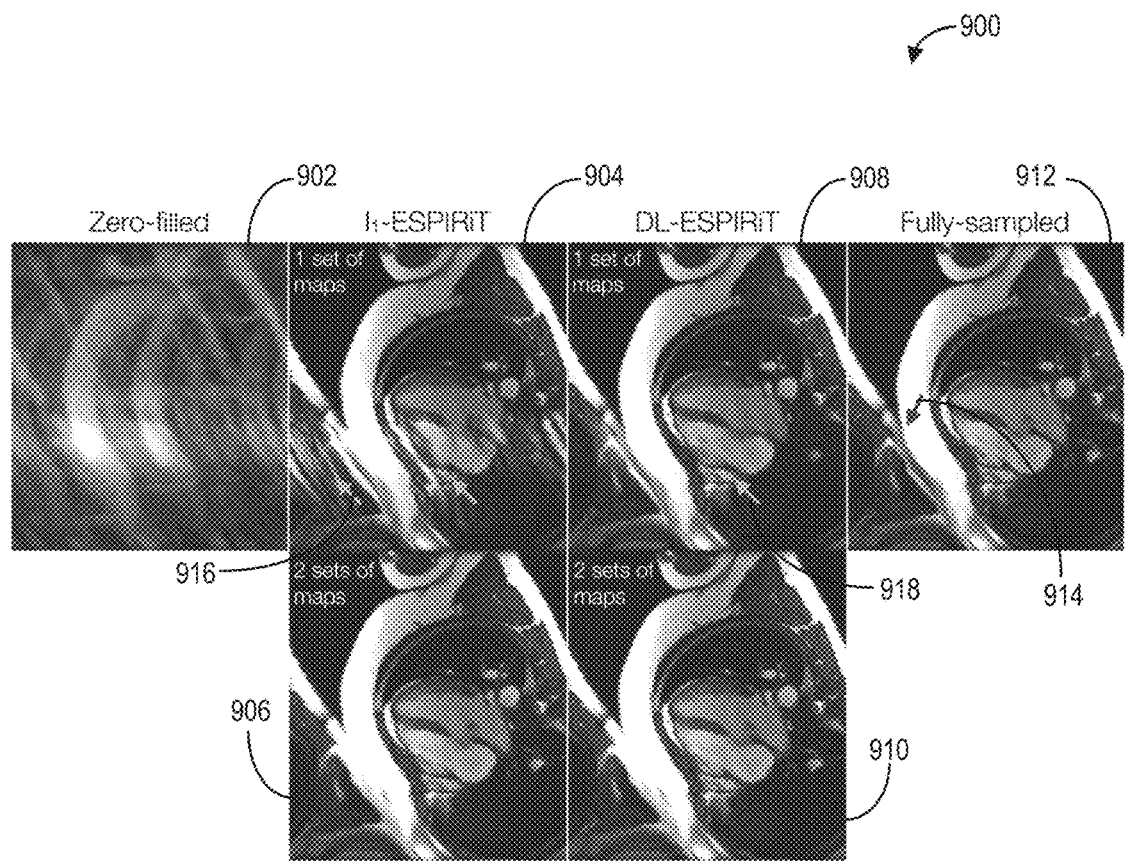
FIG. 9 shows a second set of cardiac MR images reconstructed by different techniques.
Figure 10:
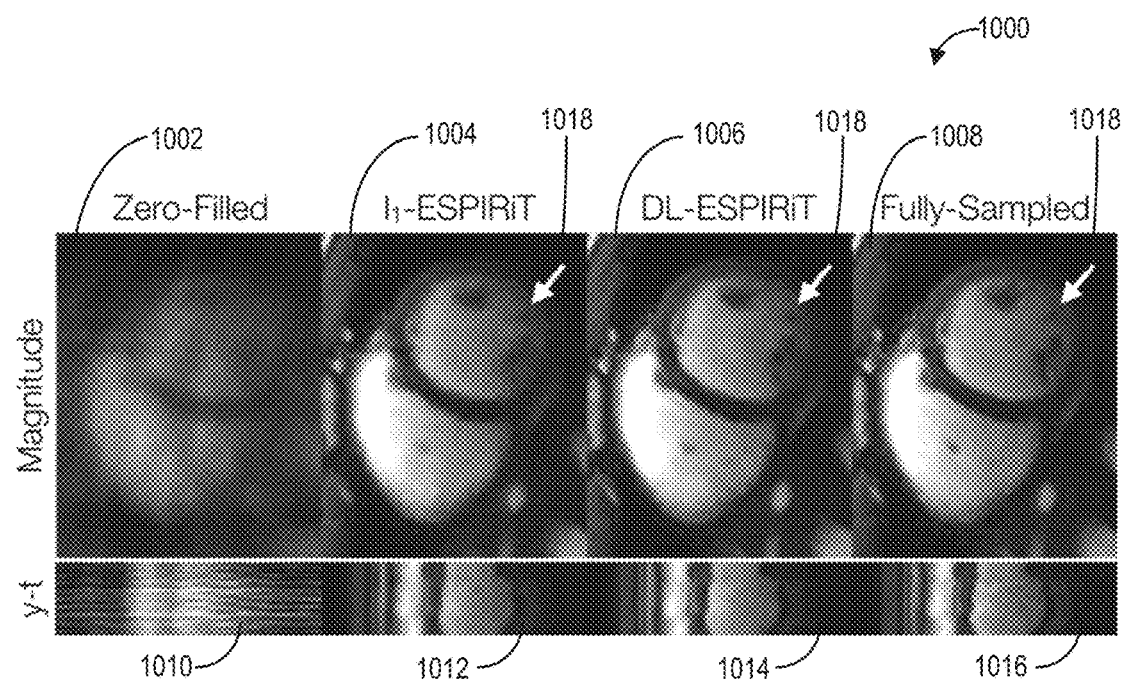
FIG. 10 shows a third set of cardiac MR images reconstructed by different techniques.

The present disclosure describes methods and systems for reconstructing MR images from undersampled MRI data using a deep learning-based framework that utilizes an extended coil sensitivity model to overcome model errors, such as those caused by anatomy overlap. Undersampled k-space data may be acquired, during an MRI scan, with an MRI apparatus, such as the MRI apparatus shown in FIG. 1. The MRI apparatus may include one or more multi-coil receiver arrays each including a plurality of RF coils, such as the example RF coil arrays shown in FIG. 2. During the MRI scan, each receiver coil may acquire partial k-space data (due to undersampling to accelerate scan times). As shown in the example process flow of FIG. 3, the raw k-space data may be used to reconstruct multiple initial MR images and multiple coil sensitivity maps, using an ESPIRiT calibration. The multiple initial MR images and maps are then input in a deep neural network (referred to herein as DL-ESPIRiT). The DL-ESPIRiT network reconstructs multiple MR images in an iterative fashion and outputs multiple final reconstructed MR images at the end of iteration, each corresponding to a different map of the multiple sets of sensitivity maps. These final reconstructed MR images may then be combined to one MR image and displayed to a user and used for diagnosis, as shown in the example method of FIG. 6. Further details of an example DL-ESPIRiT network are shown in FIGS. 4-5. The DL-ESPIRiT network may be trained, end-to-end, by inputting artifact-free ground truth MR images and corresponding initial MR images reconstructed directly from undersampled MR data or augmented by simulated artifacts into the DL-ESPIRiT network, as shown in the example method of FIG. 7. Example MR images having various levels of different imaging artifacts, which are reconstructed via different reconstruction techniques, including the DL-ESPIRiT technique, are shown in FIGS. 8-10.

Figure 1:
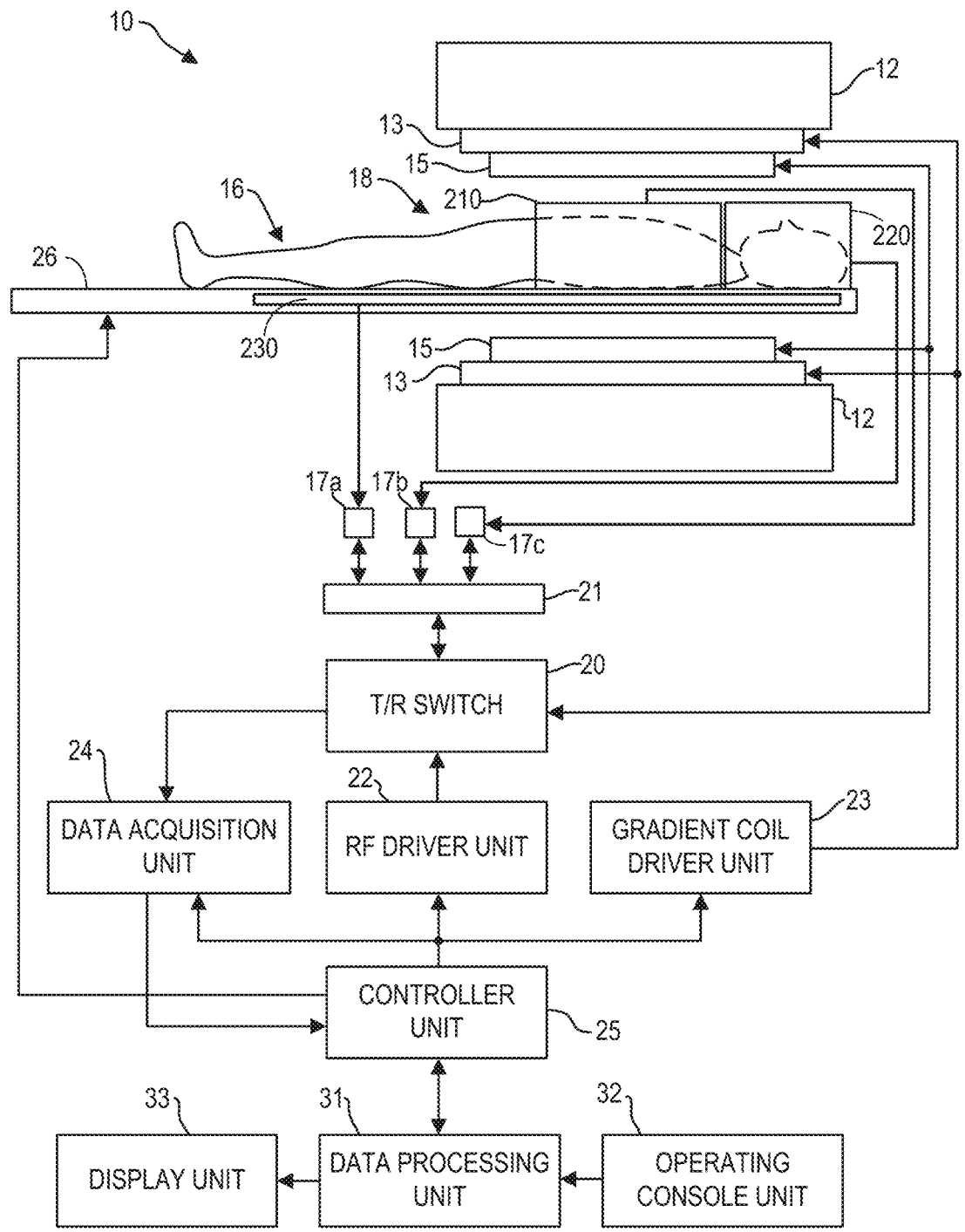
FIG. 1 is a block diagram of a magnetic resonance imaging (MRI) system, according to an exemplary embodiment.

FIG. 1 illustrates a magnetic resonance imaging (MRI) apparatus 10 that includes a magnetostatic field magnet unit 12, a gradient coil unit 13, one or more local RF coil arrays (210, 220, and 230), an RF body coil unit 15, a transmit/receive (T/R) switch 20, an RF port interface 21, an RF driver unit 22, a gradient coil driver unit 23, a data acquisition unit 24, a controller unit 25, a patient bed 26, a data processing unit 31, an operating console unit 32, and a display unit 33. The MRI apparatus 10 transmits electromagnetic pulse signals to a subject 16 placed in an imaging space 18 with a magnetostatic field formed to perform a scan for obtaining magnetic resonance (MR) signals from the subject 16 to reconstruct an image of the slice of the subject 16 based on the MR signals thus obtained by the scan.

The magnetostatic field magnet unit 12 includes, for example, typically an annular superconducting magnet, which is mounted within a toroidal vacuum vessel. The magnet defines a cylindrical space surrounding the subject 16, and generates a constant primary magnetostatic field $B_0$.

The MRI apparatus 10 also includes a gradient coil unit 13 that forms a gradient magnetic field in the imaging space 18 so as to provide the magnetic resonance signals received by the RF coil arrays with three-dimensional positional information. The gradient coil unit 13 includes three gradient coil systems, each of which generates a gradient magnetic field which inclines into one of three spatial axes perpendicular to each other, and generates a gradient field in each of frequency encoding direction, phase encoding direction, and slice selection direction in accordance with the imaging condition. More specifically, the gradient coil unit 13 applies a gradient field in the slice selection direction (or scan direction) of the subject 16, to select the slice; and the RF body coil unit 15 or the local RF coil arrays may transmit an RF pulse to a selected slice of the subject 16. The gradient coil unit 13 also applies a gradient field in the phase encoding direction of the subject 16 to phase encode the magnetic resonance signals from the slice excited by the RF pulse. The gradient coil unit 13 then applies a gradient field in the frequency encoding direction of the subject 16 to frequency encode the magnetic resonance signals from the slice excited by the RF pulse.

Three local RF coil arrays 210, 220, and 230 are also shown in FIG. 1. The local RF coil arrays are disposed, for example, to enclose the region to be imaged of the subject 16. In the static magnetic field space or imaging space 18 where a static magnetic field $B_0$ is formed by the magnetostatic field magnet unit 12, the local RF coil arrays may transmit, based on a control signal from the controller unit 25, an RF pulse that is an electromagnet wave to the subject 16 and thereby generates a high-frequency magnetic field $B_1$. This excites a spin of protons in the slice to be imaged of the subject 16. The local RF coil arrays receive, as a MR signal, the electromagnetic wave generated when the proton spin returns into alignment with the initial magnetization vector. In one embodiment, each local RF coil may transmit and receive an RF pulse using the same local RF coil. In another embodiment, the local RF coil may be used for only receiving the MR signals, but not transmitting the RF pulse. Details of the local RF coil arrays are presented in FIG. 2.

The RF body coil unit 15 is disposed, for example, to enclose the imaging space 18, and produces RF magnetic field pulses $B_1$ orthogonal to the main magnetic field $B_0$ produced by the magnetostatic field magnet unit 12 within the imaging space 18 to excite the nuclei. In contrast to the local RF coil arrays (such as local RF coil arrays 210 and 220), which may be easily disconnected from the MRI apparatus 10 and replaced with another local RF coil, the RF body coil unit 15 is fixedly attached and connected to the MRI apparatus 10. Furthermore, whereas the local coil arrays can transmit to or receive signals from only a localized region of the subject 16, the RF body coil unit 15 generally has a larger coverage area and can be used to transmit or receive signals to the whole body of the subject 16. Using receive-only RF coil arrays and transmit body coils provides a uniform RF excitation and good image uniformity at the expense of high RF power deposited in the subject. For a transmit-receive RF coil array, the coil array provides the RF excitation to the region of interest and receives the MR signal, thereby decreasing the RF power deposited in the subject. It should be appreciated that the particular use of the local RF coil arrays and/or the RF body coil unit 15 depends on the imaging application.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect one or more of the local RF coil arrays to the data acquisition unit 24 when the local RF coil arrays operate in receive mode, and to the RF driver unit 22 when operating in transmit mode. When the local RF coil arrays and the RF body coil unit 15 are both used in a single scan, for example if the local RF coil arrays are configured to receive MR signals and the RF body coil unit 15 is configured to transmit RF signals, then the T/R switch 20 may direct control signals from the RF driver unit 22 to the RF body coil unit 15 while directing received MR signals from the local RF coil arrays to the data acquisition unit 24. The RF body coil unit 15 may be configured to operate in a transmit-only mode, a receive-only mode, or a transmit-receive mode. The local RF coil arrays may be configured to operate in a transmit-receive mode or a receive-only mode.

The RF driver unit 22 includes a gate modulator (not shown), an RF power amplifier (not shown), and an RF oscillator (not shown) that are used to drive the RF coil arrays and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil arrays.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a preamplifier (not shown), a phase detector (not shown), and an analog/digital converter (not shown) used to acquire the MR signals received by the local RF coil arrays. In the data acquisition unit 24, the phase detector phase detects, using the output from the RF oscillator of the RF driver unit 22 as a reference signal, the MR signals received from the RF coil arrays and amplified by the preamplifier, and outputs the phase-detected analog magnetic resonance signals to the analog/digital converter for conversion into digital signals. The digital signals thus obtained are output to the data processing unit 31.

The MRI apparatus 10 includes a table 26 for placing the subject 16 thereon. The subject 16 may be moved inside and outside the imaging space 18 by moving the table 26 based on control signals from the controller unit 25. One or more of the RF coil arrays may be coupled to the table 26 and moved together with the table.

The controller unit 25 includes a computer and a recording medium on which a program to be executed by the computer is recorded, in some embodiments. The program when executed by the computer causes various parts of the apparatus to carry out operations corresponding to predetermined scanning. The recording medium may comprise, for example, a ROM, flexible disk, hard disk, optical disk, magneto-optical disk, CD-ROM, or non-volatile memory card. The controller unit 25 is connected to the operating console unit 32 and processes the operation signals input to the operating console unit 32 and furthermore controls the table 26, RF driver unit 22, gradient coil driver unit 23, and data acquisition unit 24 by outputting control signals to them. The controller unit 25 also controls, to obtain a desired image, the data processing unit 31 and the display unit 33 based on operation signals received from the operating console unit 32.

The operating console unit 32 includes user input devices such as a keyboard and a mouse. The operating console unit 32 is used by an operator, for example, to input such data as an imaging protocol and to set a region where an imaging sequence is to be executed. The data about the imaging protocol and the imaging sequence execution region are output to the controller unit 25.

The data processing unit 31 includes a computer and a recording medium on which a program to be executed by the computer to perform predetermined data processing is recorded. The data processing unit 31 is connected to the controller unit 25 and performs data processing based on control signals received from the controller unit 25. The data processing unit 31 is also connected to the data acquisition unit 24 and generates spectrum data by applying various image processing operations to the magnetic resonance signals output from the data acquisition unit 24.

The display unit 33 includes a display device and displays an image on the display screen of the display device based on control signals received from the controller unit 25. The display unit 33 displays, for example, an image regarding an input item about which the operator inputs operation data from the operating console unit 32. The display unit 33 also displays a slice image of the subject 16 generated by the data processing unit 31.

The MRI apparatus 10 may be configured with a deep neural system, or network, for reconstructing MR images from undersampled k-space data acquired via multiple receiver coils of the MRI apparatus 10. For example, a trained deep neural network may be stored at the data processing unit 31. In some embodiments, the deep neural network may be implemented on an edge device (not shown) connected to the MRI apparatus 10. In some embodiments, the deep neural network may be implemented remotely, for example in a cloud in communication with the MRI apparatus 10. In some embodiments, portions of the deep neural network are implemented on different devices, such as any appropriate combination of the MRI apparatus 10, the edge device, the cloud, etc.

Different RF coil arrays may be utilized for different scanning objectives. To that end, one or more the RF coil arrays, such as RF coil array 210, may be disconnected from the MRI apparatus 10, so that a different coil array may be connected to the MRI apparatus 10. The RF coil arrays may be coupled to the T/R switch 20, and thus to the RF driver unit 22 and the data acquisition unit 24, via a connector and an RF port interface 21. Each RF coil array may be electrically coupled to one or more connectors (such as connector 17a-17c). The connector(s) may be plugged into the RF port interface 21 to electronically couple the RF coil array to the T/R switch 20. For example, coil array 210 may be electronically coupled to the MRI apparatus 10 by plugging connector 17c into RF port interface 21. As such, the local RF coil arrays may be easily changed.

Figure 2:
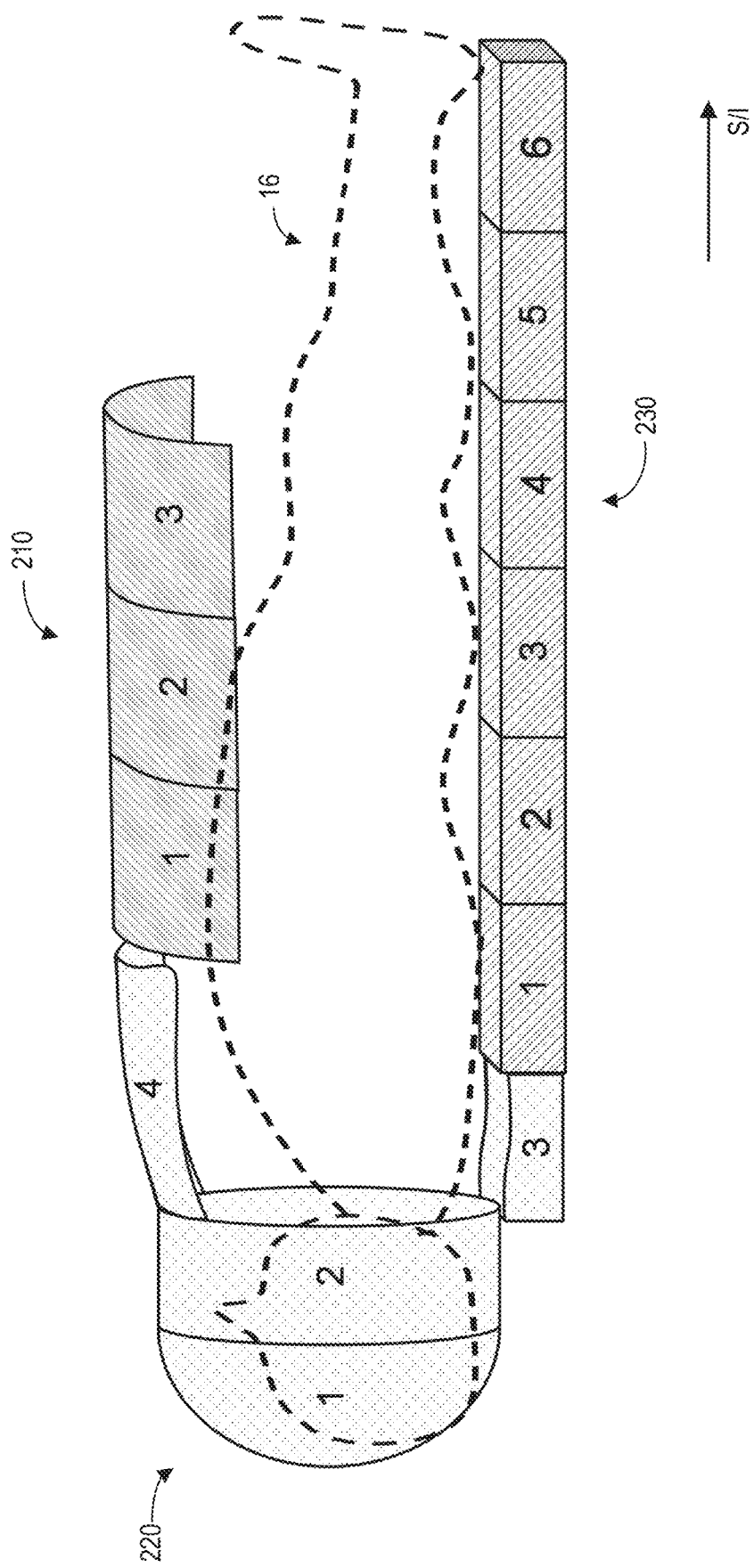
FIG. 2 is a schematic arrangement of radio frequency (RF) coil arrays relative to an imaging subject, according to an exemplary embodiment.

FIG. 2 shows an example arrangement of RF coil arrays of the MRI apparatus 10 of FIG. 1 relative to the subject 16.

In particular, an anterior coil array 210, a head-neck coil array 220, and a posterior coil array 230 are positioned on top of the body, over the head-neck, and under the body, respectively. Each coil array is an individual piece and may be physically separated from each other. One or more of the coil arrays (such as the anterior coil array 210 and head-neck coil array 220) may be connected or removed from the MRI apparatus 10 by the operator. The posterior coil array 230 may be embedded within and moved together with table 26. Each coil array may include a plurality of coil elements, and each coil element receives MR signals generated from a specific volume of the subject 16.

Each coil element of the coil arrays is electronically coupled to the controller unit (such as controller unit 25 of FIG. 1) via a channel. In particular, each coil element can sense the MR signals and transfer the MR signal to the data acquisition unit (such as data acquisition unit 24 of FIG. 1) of the MRI apparatus via the corresponding channel. The data acquisition unit then outputs digitized MR signals to the controller unit. In some examples, each individual coil element may be coupled to one channel, and each channel may only be coupled to one coil element (e.g., anterior coil array 210 may include 12 coil elements coupled to the data acquisition unit via 12 separate channels). In other examples, more than coil element may be coupled to a given channel (e.g., anterior coil array 210 may include 12 coil elements coupled to the data acquisition unit via 6 separate channels).

The MR signals acquired from the various RF coil arrays are collected in a grid of raw data, known as k-space. K-space is an array of numbers representing spatial frequencies in the MR image. In parallel imaging, the signals from multiple receiver coils (e.g., RF coil arrays), are processed simultaneously "in parallel" along separate channels. To reduce scan times in parallel imaging, the number of phase encoding steps is reduced by acquiring only partial k-space MR data (e.g., only half the lines in k-space are filled). This may be referred to herein as undersampling MRI data. Each coil exhibits a different spatial sensitivity profile, which acts as an additional spatial encoding function, and can be used to accelerate the acquisition by subsampling (e.g., undersampling) k-space and reconstructing images by using the sensitivity information. Various reconstruction techniques or algorithms, in the image domain (e.g., SENSE) or k-space domain (e.g., GRAPPA), may be implemented to estimate the missing lines of k-space and correct the aliasing overlap in parallel imaging images. These techniques may accelerate scan times by reducing the amount of data collection without aliasing. ESPIRiT combines SENSE and GRAPPA to inherit benefits from both techniques.

Figure 3:
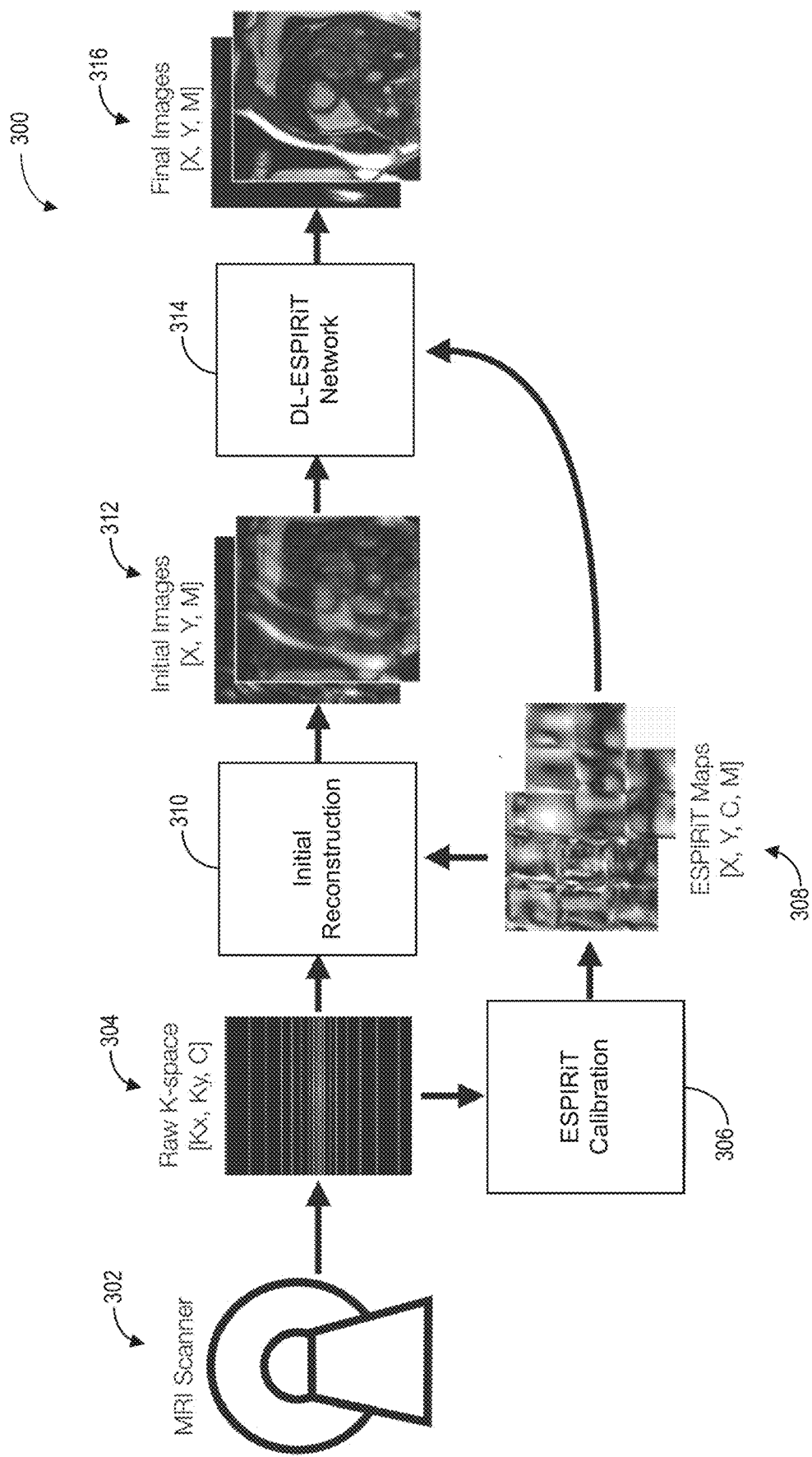
FIG. 3 shows a schematic diagram illustrating an example process flow for reconstructing MRI images using a deep learning-ESPIRiT network, according to an embodiment.

Referring to FIG. 3, a schematic diagram illustrating an example process flow 300 for reconstructing MRI images using a deep learning (DL)-ESPIRiT network (also referred to herein as a deep learning and extended coil sensitivity network) is shown according to an exemplary embodiment. The process flow begins at 302 where a patient is put inside an MRI scanner (which may be similar to MRI apparatus 10 shown in FIG. 1) and a scan of the patient using a multi-coil receiver array of the MRI scanner is performed. The DL-ESPIRiT technique discussed herein allows for flexibility in modifying the imaging model used to acquire data during the MRI scan. For example, the imaging model may incorporate off-resonance information, a signal decay model, k-space symmetry with homodyne processing, and arbitrary sampling trajectories (e.g., radial, spiral, hybrid encoding, and the like). The MR signals acquired from the multi-coil receiver array are collected as raw, k-space data, as shown at 304. The k-space data at 304 may include a number of MR signals along a Kx and Ky axis, which are the spatial frequency dimensions, for a total number C of receiver coils (or groups of receiver coils) used to acquire the data. Additionally, k-space is only partially filled due to undersampling. In some embodiments, the k-space center is more densely sampled than other regions of the k-space, for the purpose of autocalibration.

The ESPIRiT calibration is performed at 306, directly on the raw k-space data in order to estimate multiple sets of coil sensitivity maps (e.g., ESPIRiT maps), as output at 308. The ESPIRiT calibration includes generating explicit coil sensitivity maps from autocalibration data collected at an autocalibration region (e.g., center of k-space). In particular, this includes assembling the raw k-space data into a matrix (known as the calibration matrix) using a sliding window throughout the autocalibration region. Each block inside the autocalibration region is a row in the calibration matrix, and columns of the calibration matrix are shifted versions of the autocalibration region. Then an ESPIRiT reconstruction operator is generated from the right singular vectors of the calibration matrix, and the sensitivity maps which are the eigenvectors of the reconstruction operator are computed via eigenvalue decomposition, each map corresponding to one set of eigenvectors. Details of the ESPIRiT calibration can be found in "ESPIRiT—An eigenvalue approach to autocalibrating parallel MRI: Where SENSE meets GRAPPA," M. Uecker et al., Magnetic Resonance in Medicine, vol. 71, no. 3, pp. 990-1001, 2014.

The number of sets of sensitivity maps is determined according to the number of eigenvectors computed from the eigenvalue decomposition. In the ideal case, there is only a single eigenvector corresponding to the absolute eigenvalue of "1" at each location and all other eigenvalues are <<1. However, errors in the acquisition may lead to multiple eigenvectors corresponding to the absolute eigenvalue of "1" or additional eigenvalues smaller than but close to "1." The number of sensitivity maps used in reconstruction is a hyperparameter set prior to reconstruction. In some embodiments, two sets of sensitivity maps are used in the reconstruction to reduce anatomy overlaps.

The multiple sets of ESPIRiT maps are output at 308. The ESPIRiT maps are coil sensitivity maps which present a visualization of the relative weight of each coil across the spatial dimensions, X and Y, of the image. It should be understood that although 2D images are used herein as an example for illustration, the method can be applied to 3D images. Each set of coil sensitivity maps (one map for each coil) corresponds to one MR image that is reconstructed. As shown in FIG. 3, two coil sensitivity maps (e.g., M=2) are generated at 308. However, in alternate embodiments, more than two coil sensitivity maps may be generated at 308.

At 310, an initial reconstruction of MR images is performed from the raw k-space data acquired at 304 and the multiple sets of coil sensitivity maps output at 308. For example, the process at 310 may include reconstructing multiple MR images from the undersampled k-space data and the multiple sets of coil sensitivity maps, where each initial reconstructed MR image output at 312 corresponds to a different set of the multiple sets of coil sensitivity maps. These initial MR images may be zero-filled images reconstructed based on the undersampled k-space data alone, without filling in the missing lines of k-space. Thus, the initial MR images reconstructed at 310 and output at 312 are relatively fast to compute and may be heavily aliased.

The initial MR images (two shown in the example of FIG. 3) output at 312 are then input, along with the multiple sets of coil sensitivity maps output at 308, into the DL-ESPIRiT network at 314, which may also be referred to herein as the deep learning and extended coil sensitivity network or framework. Details on the DL-ESPIRiT network are shown in FIGS. 4 and 5, as discussed further below. Generally, the DL-ESPIRiT network at 314 includes a deep neural network (which may be a convolutional neural network, in one embodiment) interspersed with data consistency layers which utilize the multiple sets of coil sensitivity maps.

In a conventional ESPIRiT reconstruction, a set of MR images 2, each corresponding to a set of coil sensitivity maps, can be estimated from raw undersampled measurements y by solving a non-linear inverse problem of the form:

$$\hat{x} = \underset{x}{\operatorname{argmin}} \|y - Ax\|_2^2 + \lambda R(x), \quad \text{(Equation 1)}$$

where A is comprised of multiple sets of coil sensitivity maps, the discrete Fourier transform, and the k-space sampling operator. The regularization function R and associated regularization factor are typically chosen to be an $l_1$-norm for balancing between data consistency and prior knowledge of the image content (i.e., the prior). Generally, if R is a proper convex function, then the optimization problem in Equation 1 can be iteratively solved using the proximal gradient descent algorithm:

$$x^{(k+1)} = S_R(x^{(k)} - A^H(Ax^{(k)} - y)), \quad \text{(Equation 2)}$$

where $A^H$ is the conjugate transpose of A, and $S_R$ is defined as the proximal operator of the regularization function R. In the case that R is the $l_1$-norm of x, the update rule in Equation 2 simplifies into the iterative shrinkage thresholding algorithm (ISTA).

In this disclosure, the prior on the set of images x is modeled with a convolutional neural network (CNN), as shown in FIG. 3, which replaces the proximal operation $S_R$ in Equation 2. This gives the following equation for the DL-ESPIRiT network:

$$x^{(k+1)} = \text{CNN}^{(k)}(x^{(k)} - A^H(Ax^{(k)} - y)), \quad \text{(Equation 3)}$$

The prior information is then implicitly learned by unrolling Equation 3 and trained end-to-end as a deep CNN. Network weights are allowed to vary between unrolled iterations to enhance the network's representational power. The network is summarized in FIG. 4 and expanded on in more detail in FIG. 5. As shown in FIG. 3, the final reconstructed MR images (one corresponding to each set of coil sensitivity maps) at the end of the iteration are output from the DL-ESPIRiT network at 316. These final reconstructed MR images can then be combined to be one image which has reduced artifacts (e.g., anatomy overlap, motion, chemical shift, distortion, gradient non-linearity, and the like) compared to other reconstruction techniques, as explained further below with reference to FIGS. 8-10.

Turning to FIG. 4, a schematic diagram 400 of the DL-ESPIRiT network 314 and its inputs and outputs are shown, according to an exemplary embodiment. The inputs (initial MR images 312 and multiple sets of coil sensitivity maps (e.g., ESPIRiT maps) 308) and outputs (final reconstructed MR images 316) shown in FIG. 4 are the same as those shown in FIG. 3. As discussed above, two initial MR images 312 are input and processed simultaneously through the DL-ESPIRiT network 314 and two final reconstructed MR images 316 are output. Each of the input and output MR images corresponds to a different set of the multiple sets of coil sensitivity maps. By having multiple ESPIRiT maps and MR images, the network may split up overlapping anatomy components in the MR images, as denoted by arrows 406, and de-alias them separately. In alternate embodiments, there may be more than two sets of MR images and coil sensitivity maps (such as three, four, or the like).

The DL-ESPIRiT network 314 includes a convolutional neural network (CNN) 402 and data consistency (DC) layer 404 which are iteratively applied for a number of iterations (N). The number of iterations N can be, for example, 5, 10, 20, or any other appropriate number. The CNN and DC layer work together to reconstruct multiple MR images, each MR image corresponding to a set of coil sensitivity maps. The CNN 402 includes a plurality of convolutional layers, as discussed further below with reference to FIG. 5. The CNN 402 may also be referred to as denoising blocks. The DC layer 404 enforces consistency between input k-space data and intermediate outputs of the denoising blocks (CNN 402). This ensures that the final MR image is consistent with measured data points and consequently minimizes the chance of hallucinations. The DC layers 404 use the multiple sets of coil sensitivity maps to project back and forth between k-space and image domains. The entire DL-ESPIRiT network 314 is trained end-to-end on a loss between the output and ground truth (e.g., fully-sampled) MR images, as explained further below with reference to FIG. 7.

A layout of the DL-ESPIRiT network 314 is shown in FIG. 5, according to an exemplary embodiment. In particular, FIG. 5 shows a single iteration of the DL-ESPIRiT network 314 with details of the CNN 402 architecture. A number of input and output images for each convolutional layer of the CNN 402 are shown above each convolution block in FIG. 5. It should be noted that the numbers shown in FIG. 5 are exemplary and different numbers of images than those shown may be output from one convolutional layer and input into the next convolutional layer.

As shown in FIG. 5, the complex-valued MR images (e.g., input images 312) are split into real part images 502 and imaginary part images 504. The DL-ESPIRiT network described herein accommodates the reconstruction of multiple sets of images at once. In the case of two sets of ESPIRiT maps, as shown in FIGS. 3-5, four input images (two real images 502 and two imaginary images 504) are passed through a series of convolutional layers 506 and transformed into feature maps. After each convolutional layer, feature maps are passed through non-linear activation layers 508. To accelerate training convergence and reduce vanishing gradient issues, residual connections 510 are placed in between couples of convolutions. At the end of each iteration, a final convolution 512 is applied to transform from feature maps back to images in order to apply the DC layer 404. The weights of the convolutional layers 506 are learned during training, as discussed further below. In an example, the DL-ESPIRiT network has 10 iterations, 2 ResNet blocks per iteration, size-3×3 spatial filters, size-3 temporal filters, and filter depths of 64.

Additionally, the initial convolutional layer in each unrolled iteration accepts multiple complex images, each corresponding to a set of coil sensitivity maps. Each MR image 312, which is split up into real and imaginary components, is stacked as a corresponding channel. Convolutions then share information between all channels, allowing them to exploit correlations between these multiple sets of images on a data-driven basis. In contrast, conventional $l_1$-ESPIRiT treats each set of images separately during iterations and is not able to correlate the multiple sets of images.

In contrast to other DL-based reconstruction approaches, convolutional layers 506 are modified to learn extra filters (increased filter depth) in order to reconstruct multiple images at once. This is demonstrated in FIG. 5 where the first convolutional layer of the CNN accepts 4 channels (one real component and one imaginary component for each image to be reconstructed) instead of 2 channels. In this way, multiple MR images may be simultaneously reconstructed.

FIG. 5 shows one embodiment of a neural network used in the DL-ESPIRiT network 314 for illustration, not for limitation. In alternate embodiments, a different neural network architecture may be used for the DL-ESPIRiT network described herein. For example, different neural network structures may include residual networks (ResNets), U-Nets, autoencoder, recurrent neural networks, and fully connected networks. In yet other embodiments, the individual convolution and activation layers of the neural network may also be modified to natively support complex-valued data.

Figure 6:
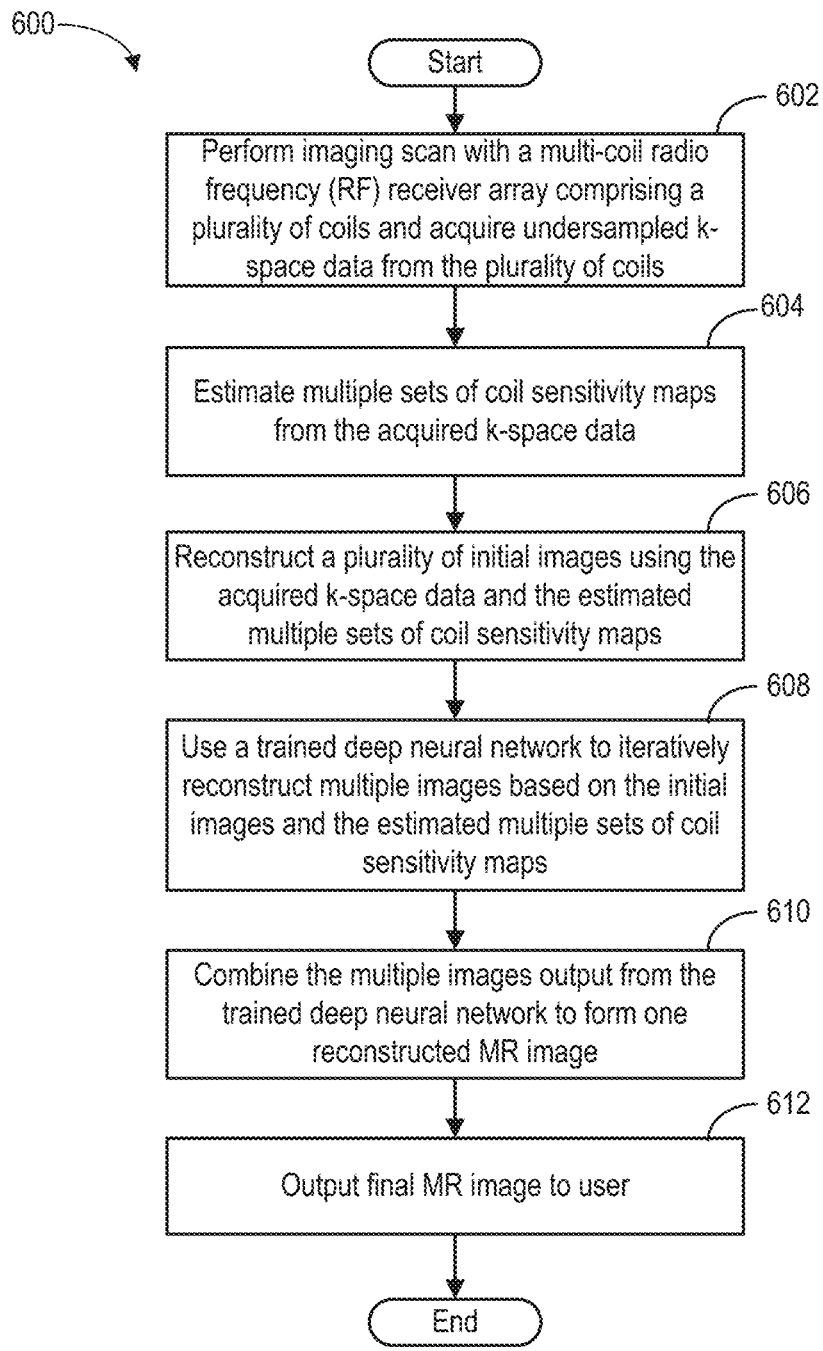
FIG. 6 shows a flow chart of a method for reconstructing MR images from undersampled k-space data acquired from a plurality of MRI coil elements using a deep neural network, according to an exemplary embodiment.

FIG. 6 shows a flow chart of a method 600 for reconstructing multiple MR images with reduced artifacts from undersampled k-space data acquired from a multi-coil array using a deep neural network. The deep neural network may be the deep learning (DL)-ESPIRiT network discussed above with reference to FIGS. 3-5. As discussed further below, each of the final reconstructed MR images corresponds to a different set of coil sensitivity maps, where multiple sets of coil sensitivity maps (referred to herein as ESPIRiT maps) are input into and used within the DL-ESPIRiT network. FIG. 6 is described with regard to the systems, components, and networks of FIGS. 1-5, though it should be appreciated that the method 600 may be implemented with other systems, components, and networks without departing from the scope of the present disclosure. In some embodiments, method 600 may be implemented as executable instructions in any appropriate combination of the MRI apparatus 10, an edge device connected to the MRI apparatus 10, a cloud in communication with the MRI apparatus, and so on. As one example, method 600 may be implemented in non-transitory memory of a computing device, such as the controller unit (e.g., processor) of the MRI apparatus 10 in FIG. 1.

Method 600 begins at 602 by performing an imaging scan using a multi-coil radio frequency (RF) receiver array comprising a plurality of coil elements and acquiring undersampled k-space data from the multi-coil receiver array. In one example, the method at 602 includes performing an MRI scan with MRI apparatus 10 shown in FIG. 1 and acquiring undersampled k-space data with the multi-coil receiver array of the MRI apparatus, as described above with reference to FIG. 1. An example of the acquired, undersampled k-space data is shown at 304 in FIG. 3. As described above with reference to FIG. 3, the MR signals acquired from the multi-coil receiver array are collected as raw, k-space data which includes a number of MR signals for a total number of receiver coils (or groups of receiver coils) used to acquire the data. K-space is only partially filled due to undersampling. In some embodiments, the k-space center is more densely sampled than other regions of the k-space, for the purpose of autocalibration.

This undersampling may significantly reduce scan times (e.g., the time to acquire the k-space data for reconstructing MR images); however, zero-filled MR images reconstructed from this undersampled data may have significant aliasing effects, thereby reducing image quality and the ability of a medical professional to make a diagnosis based on the resulting images. Thus, a parallel processing method for reconstructing images of higher quality, with reduced imaging artifacts, may be applied to the undersampled k-space data, as described further below.

At 604, the method includes estimating multiple sets of coil sensitivity maps (also referred to herein as ESPIRiT maps) from the acquired k-space data. In one embodiment, the method at 604 may include performing an ESPIRiT calibration directly on the raw k-space data acquired at 602 in order to estimate the multiple sets of coil sensitivity maps. As explained above with reference to 306 in FIG. 3, performing the ESPIRiT calibration includes generating explicit coil sensitivity maps from autocalibration data collected at an autocalibration region (e.g., k-space center) using eigenvalue decomposition. The multiple sets of coil sensitivity maps generated at 604 may include at least two sets of coil sensitivity maps, where each set of coil sensitivity maps includes a sensitivity map for each coil (or grouping of coils) used to acquire the k-space data.

At 606, the method includes reconstructing a plurality of initial images (e.g., MR images) using the acquired k-space data (acquired at 602) and the estimated multiple sets of coil sensitivity maps (estimated at 604). Each of the initial images may be initial MR images that each correspond to a different set of the multiple sets of sensitivity maps. Thus, the number of initial MR images reconstructed at 606 is equal to the number of sets of coil sensitivity maps estimated at 604. The method at 606 may follow the method outlined above with reference to 310 of FIG. 3. The initial reconstructed MR images may be zero-filled images with pronounced aliasing due to being reconstructed from partial (e.g., undersampled) k-space data.

The method proceeds to 608 to use a trained deep neural network to iteratively reconstruct multiple images based on the initial images and the estimated multiple sets of coil sensitivity maps. For example, the method at 608 may include inputting the initial images and the multiple sets of coil sensitivity maps into the deep neural network. In one example, the deep neural network may be the DL-ESPIRiT network shown in FIGS. 3-5, as described above. The method then includes, using the deep neural network, iteratively reconstructing multiple images (e.g., multiple MR images), each reconstructed image corresponding to a different set of the multiple sets of coil sensitivity maps. In one example, the method at 308 may include applying the DL-ESPIRit network to the input initial MR images and the multiple sets of coil sensitivity maps for a plurality of iterations. As described above, the DL-ESPIRiT network may include a convolutional neural network (CNN) integrated with a data consistency (DC) layer in which a plurality of convolutions are performed on the input images (separated into real and imaginary components) and then the data consistency layer is applied to enforce consistency between input k-space data and output images. Further details of an example DL-ESPIRiT network are described above with reference to FIGS. 3-5. The network runs a plurality of iterations, until images with reduced imaging artifacts (e.g., within a pre-set error threshold) are output from the network. The number of iterations may be chosen and fixed prior to training. As one example, the optimal number of iterations may be found by trial-and-error experiments. For example, at inference time, the network may apply the same number of iterations that it was fixed to apply during the training stage. Applying the DL-ESPIRiT network at 608 includes simultaneously reconstructing multiple MR images. This allows the network to split up overlapping anatomy components in the multiple MR images and de-alias the overlapping anatomy components separately.

At 610, the method includes combining the multiple MR images output from the trained deep neural network to form one reconstructed MR image.

Combination of the final reconstructed images into the final combined reconstructed MR image could be done using a root-sum-of-squares approach:

$$I_{RSS} = \sqrt{\sum_{k=1}^{N} I_k^2} \qquad \text{(Equation 4)}$$

The method may then continue to 612 to output (e.g., display) the final combined reconstructed MR image to a user. In one example, outputting the final combined reconstructed MR image includes displaying the final combined reconstructed MR image to a user via a display screen of a display device. In one example, the display device is display unit 33 of MRI apparatus 10 shown in FIG. 1. In another example, outputting the final combined reconstructed MR image may additionally or alternatively include storing the final combined reconstructed MR image on a memory connected with the processor so that a user may access and process the stored image at a later time. A medical professional may then use the displayed and stored image for diagnosis.

Figure 7:
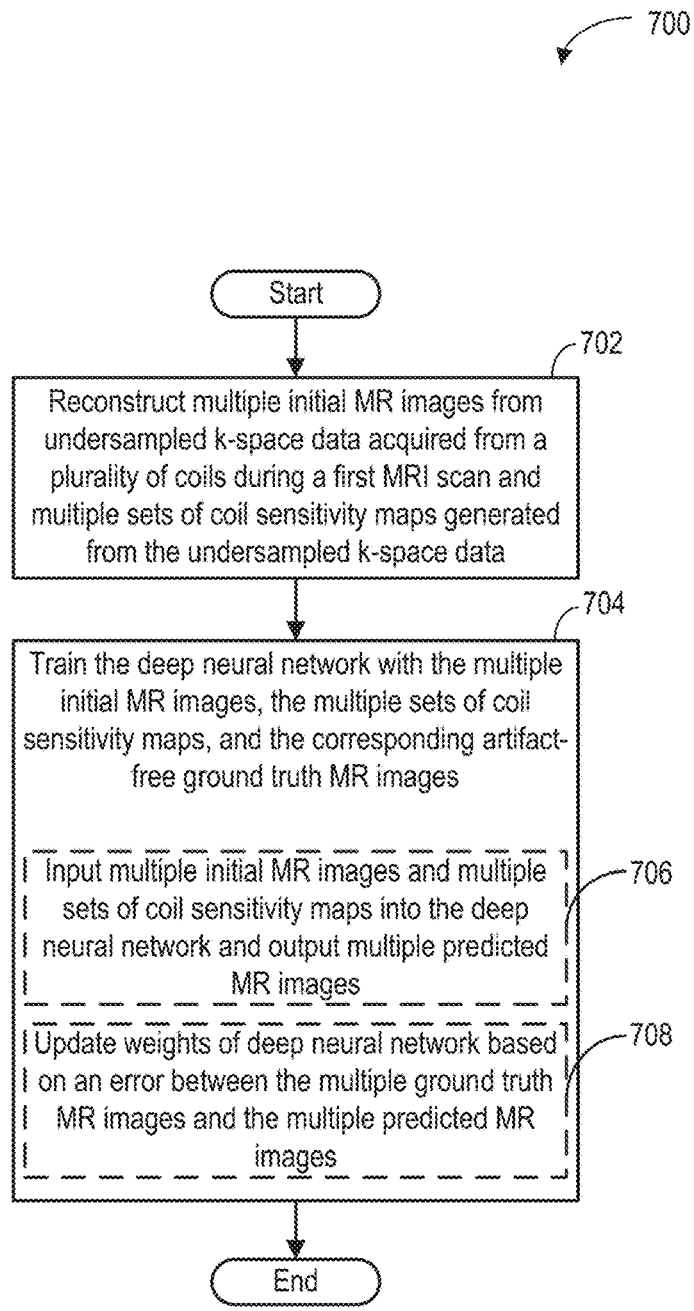
FIG. 7 show a flow chart of a method for training the deep neural network used in the method of FIG. 6, according to an exemplary embodiment.

Turning now to FIG. 7, a method 700 is shown for training the deep neural network used in method 600 of FIG. 6. As discussed above, in one example, the deep neural network may be the DL-ESPIRiT network described above with reference to FIGS. 3-5. Method 700 illustrates using one instance of data to train the DL-ESPIRiT network to reconstruct multiple MR images (each corresponding to a different set of coil sensitivity maps) in an iterative fashion, with reduced imaging artifacts, from undersampled k-space data. For example, method 700 may be repeated for a plurality of training instances. Method 700 is described with regard to the systems, components, and networks of FIGS. 1-5, though it should be appreciated that the method 700 may be implemented with other systems, components, and networks without departing from the scope of the present disclosure. In some embodiments, method 700 may be implemented as executable instructions in any appropriate combination of the MRI apparatus 10, an edge device connected to the MRI apparatus 10, a cloud in communication with the MRI apparatus, and so on. As one example, method 700 may be implemented in non-transitory memory of a computing device, such as the controller unit (e.g., processor) of the MRI apparatus 10 in FIG. 1.

Method 700 begins at 702. At 702, the method includes reconstructing multiple initial MR images from undersampled k-space data acquired from a plurality of coils (of an MRI apparatus) during a first MRI scan and multiple sets of coil sensitivity maps generated from the undersampled k-space data. In one example, the method at 702 may include performing the ESPIRiT calibration (as discussed above with reference to 306 of FIG. 3 and 604 of FIG. 6) directly on the undersampled k-space data to obtain the multiple sets of coil sensitivity maps. The undersampled k-space data may be obtained by retrospectively undersampling a set of fully sampled k-space data acquired from multiple coils of an RF coil array. The initial images may be reconstructed from the undersampled k-space data, each corresponding to a different one of the multiple sets of coil sensitivity maps. The operation at 704 may be similar to the operations at 604 and 606 in FIG. 6.

The method then continues to 704 to train the deep neural network (e.g., DL-ESPIRiT network) with the multiple initial MR images, the multiple sets of coil sensitivity maps, and multiple corresponding artifact-free ground truth MR images. In one example, the artifact-free ground truth (e.g., reference) MR images are images reconstructed from the fully-sampled k-space data from which the undersampled k-space data used at 702 were obtained. The method at 704 may include, at 706, inputting the multiple initial MR images and the multiple sets of coil sensitivity maps into the deep neural network (e.g., DL-ESPIRiT network) and outputting multiple predicted MR images. Each predicted MR image of the multiple predicted MR images corresponds to a different image of the initial MR images and a different set of the multiple sets of coil sensitivity maps.

In some embodiments, the initial MR images input at 706 may be MR images with simulated artifacts. For example, random flipping, spatial and temporal translation, cropping along readout, reducing phase FOV, partial echo, etc. can be performed on the data to simulate various imaging artifacts within the initial MR images.

The method at 704 may further include, at 708 updating weights of the deep neural network based on an error (i.e., loss) between the multiple ground truth MR images (obtained by multiplying each ground truth image by the sensitivity maps estimated using ESPIRiT) and the multiple predicted MR images. After inference, the multiple predicted MR images may be combined according to Equation 4. In this way, in one embodiment, the method at 704 includes training the DL-ESPIRiT network, end-to-end (e.g., from the inputs to the convolutional neural network through the data consistency layer), according to a difference between the predicted MR images and ground truth MR images. More specifically, in one embodiment, a loss function L (Y, Ŷ) of the training defines this comparison and is equal to the mean of squared difference of pixel values between each corresponding ground truth MR image Y and the predicted MR images Ŷ:

$$L(Y, \hat{Y}) = \frac{1}{P}\sum_{p=1}^{P} \|Y_p - \hat{Y}_p\|_2, \qquad \text{(Equation 5)}$$

where P is the number of pixels of the images Y and Ŷ. The cost function may be defined as:

$$C(w_0, w_1, \ldots, w_N) = \frac{1}{M}\sum_{m=1}^{M} L(Y, \hat{Y}), \qquad \text{(Equation 6)}$$

where M is the number of input MR images and $w_i$ are the parameters or weights of the DL-ESPIRiT network. At each instance of training, the cost defined by the cost function is calculated and the error is back-propagated to update the parameters or weights $w_i$ of the DL-ESPIRiT network:

$$w_i \leftarrow w_i + \Delta w_i. \qquad \text{(Equation 7)}$$

Specifically, the change in weight $\Delta w_i$ is calculated using a gradient descent technique to reduce the cost of the next iteration:

$$\Delta w_i = -\eta \frac{\partial C}{\partial w_i}, \qquad \text{(Equation 8)}$$

where η is the learning rate, a user-defined hyper-parameter of the DL-ESPIRiT network. After updating the weights $w_i$ of the DL-ESPIRiT network at 708, method 700 then ends. As mentioned above, method 700 relates to a single instance of training for the DL-ESPIRiT network. It should be appreciated that method 700 may thus be performed for a plurality of instances to train the DL-ESPIRiT network. Further, while one example of a loss function (Equation 4) for training the DL-ESPIRiT is presented above, different loss function may be used. For example, the different loss functions for training the DL-ESPIRiT network may include the structural similarity index (SSIM), $l_2$ norm, $l_1$ norm, and/or a combination of these different functions. Further, the DL-ESPIRiT network may be trained using perceptual or adversarial loss functions. In some embodiments, the DL-ESPIRiT network may also include a momentum term to the weight updates discussed above to accelerate training. The momentum term may be chosen adaptively iteration-to-iteration using a known method, such as the Adam technique.

Turning now to FIGS. 8-10, example images reconstructed using various reconstruction techniques and having various levels of different imaging artifacts are shown. With Institutional Review Board (IRB) approval, fully sampled balanced steady-state free precession (SSFP) 2D cardiac CINE datasets were acquired from 15 volunteers at different cardiac views and slice locations on 1.5T and 3.0T MRI scanners using a 32-channel cardiac coil. All datasets were coil compressed to 8 channels for speed and memory consideration. For training the deep neural network (i.e., DL-ESPIRiT), 12 volunteer datasets were split slice-by-slice to create 180 unique examples, which were further augmented by random flipping, spatial and temporal translation, cropping along readout, reducing phase FOV to simulate anatomy overlap, partial echo, and variable density undersampling. To compare, one DL-ESPIRiT was trained to use one set of sensitivity maps, while another DL-ESPIRiT with the same layout was trained to use two sets of sensitivity maps. Average $l_1$ loss between the network output and ground truth images was used to train the networks.

For evaluation, the remaining three volunteer datasets were retrospectively undersampled to simulate a 25-second acquisition with 10× acceleration and 25% partial echo. To compare, images were constructed slice-by-slice using zero-filled undersampled data, fully-sampled data, conventional $l_1$-ESPIRiT with spatial wavelet and temporal finite differences constraints, DL-ESPIRiT trained by one set of sensitivity maps, and DL-ESPIRiT trained by two sets of sensitivity maps, separately.

Specifically, FIG. 8 shows a first set of cardiac images 800. In particular, a first, zero-filled MR image reconstructed directly from undersampled k-space data is shown at 802 and a fourth, fully-sampled MR image reconstructed directly from fully sampled k-space data is shown at 808. A second MR image reconstructed using the traditional $l_1$-ESPIRiT (without deep learning) technique, using two sets of coil sensitivity maps, is shown at 804 and a third MR image, reconstructed using the DL-ESPIRiT discussed herein with reference to FIGS. 3-6, using two sets of coil sensitivity maps, is shown at 806. As seen in the fourth MR image 808, anatomy overlap occurred on top of the arm, which has been distorted due to gradient non-linearities, indicated by arrow 810. This caused structured, high frequency ghosting to appear in the right ventricular blood pool in the second MR image 804 ($l_1$-ESPIRiT reconstruction). However, this artifact, indicated by arrows 812, was significantly reduced by the DL-ESPIRiT reconstruction, as seen in the third MR image 806. Additional ghosting below the liver, as indicated by arrows 814, was suppressed by the DL-ESPIRiT reconstruction of the third MR image 806, as compared to the second MR image 804. As shown in FIG. 8, the third MR image 806 resulting from the DL-ESPIRiT reconstruction more closely resembles the fully-sampled fourth MR image 808 than the ESPIRiT reconstructed second MR image 804. In this way, FIG. 8 shows an example of how MR images reconstructed using the DL-ESPIRiT technique discussed herein have reduced artifacts when compared to MR images reconstructed using the traditional ESPIRiT technique (without deep learning). The DL-ESPIRiT reconstruction of the third MR image 806 is acquired and reconstructed more quickly and with less computing effort than the fully-sampled fourth MR image 808.

FIG. 9 shows a second set of cardiac images 900. A first MR image 902 is a zero-filled image directly reconstructed from undersampled k-space data. As a result, the first MR image 902 is heavily aliased. A second MR image 904 and a third MR image 906 were reconstructed from undersampled k-space data using the $l_1$-ESPIRiT technique, with the second MR image 904 being reconstructed using only one set of coil sensitivity maps and the third MR image 906 being reconstructed using two sets of coil sensitivity maps. A fourth MR image 908 and a fifth MR image 910 were reconstructed from the same undersampled k-space data using the DL-ESPIRiT technique discussed herein, with the fourth MR image 908 being reconstructed using only one set of coil sensitivity maps and the fifth MR image 910 being reconstructed using two sets of coil sensitivity maps. A sixth MR image 912 is reconstructed from fully-sampled k-space data. Anatomy overlap occurred between anterior and posterior fat tissue, as indicated by arrow 914, causing ghosting to appear across the heart, as indicated by arrows 916, in the $l_1$-ESPIRiT reconstruction of the second MR image 904 and the third MR image 906. Since the DL-ESPIRiT network was trained on fully-sampled data, it was able to reduce overlap-related ghosting, as indicated by arrow 918, in the fourth MR image 908. Ghosting was even further reduced in the fifth MR image 910, due to performing the DL-ESPIRiT reconstruction with two sets of coil sensitivity maps (as compared to only one set). As seen in FIG. 9, the fifth MR image 910 most closely resembles the fully-sampled sixth MR image 912.

FIG. 10 shows a third set of cardiac images 1000. A first MR image 1002 is a zero-filled image directly reconstructed from undersampled raw k-space data, a second MR image 1004 was reconstructed from the undersampled k-space data using the $l_1$-ESPIRiT technique, a third MR image 1006 was reconstructed from the undersampled k-space data using the DL-ESPIRiT technique discussed herein, and a fourth MR image 1008 was reconstructed from fully-sampled k-space data. Corresponding y-t profiles for each of the zero-filled, $l_1$-ESPIRiT, DL-ESPIRiT, and fully-sampled methods are shown at 1010, 1012, 1014, and 1016, respectively. As seen in FIG. 10, the DL-ESPIRiT method more accurately resolves papillary muscles, indicated by arrows 1018 in each of the second MR image 1004, the third MR image 1006, and the fourth MR image 1008, inside the left ventricle. For example, the indicated papillary muscles in the third MR image 1006 more closely resemble the papillary muscles in the fully-resolved fourth MR image 1008, while the papillary muscles in the second MR image 1004 are more blurry. Additionally, the DL-ESPIRiT y-t profile 1014 depicts motion more naturally, whereas the $l_1$-ESPIRiT y-t profile 1012 suffers from staircasing artifacts due to total variation (TV) regularization required to suppress aliasing.

While FIGS. 8-10 show example MR images for cardiac-resolved 2D cardiac imaging, the DL-ESPIRiT technique discussed herein may be extended to arbitrary dimensional data including: 2D, 3D (e.g., volumetric), respiratory-resolved, time-resolved, diffusion-encoded, velocity-encoded, displacement-encoded, and multi-echo imaging. Further, while the examples shown in FIGS. 8-10 demonstrate the DL-ESPIRiT network's robustness to anatomy overlap and gradient non-linearities, the DL-ESPIRiT technique may also be used to decrease artifacts due to other types of model errors, such as motion artifacts, chemical shift, and image distortions related to echo-planar imaging. The DL-ESPIRiT network may be trained (using the method outlined above with reference to FIG. 7) to reduce all of these artifacts with sufficient training data.

In this way, a deep neural network (e.g., the DL-ESPIRiT network) may be used to reconstruct MR images from undersampled k-space data acquired at an accelerated rate (as compared to fully-sampled data). As discussed above, the DL-ESPIRiT network combines a deep neural network reconstruction framework with an extended coil sensitivity model that utilizes multiple sets of coil sensitivity maps estimated using ESPIRiT, resulting in more robust reconstruction of highly undersampled MRI data. In one example, the DL-ESPIRiT network includes a convolutional neural network which is trained to jointly reconstruct multiple images, each image corresponding to one set of the multiple sets of coil sensitivity maps. The technical effect of simultaneously reconstructing multiple images, each image of the multiple images corresponding to a different set of multiple sets of sensitivity maps, with a deep learning and extended coil sensitivity network that uses the multiple sets of sensitivity maps and multiple initial images (e.g., zero-filled images) as inputs, is generating, in less time and using less computational effort, reconstructed MR images with reduced artifacts. Specifically, the DL-ESPIRiT method provides for robust reconstruction of MR images from highly undersampled MRI data. By providing a user with MR images with reduced artifacts, a diagnosis based on the reconstructed images may be more accurate and easier to make.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for reconstructing a magnetic resonance (MR) image, comprising:
    estimating multiple sets of coil sensitivity maps from undersampled k-space data, wherein the undersampled k-space data was acquired by a multi-coil radio frequency (RF) receiver array;
    reconstructing multiple initial images using the undersampled k-space data and the estimated multiple sets of coil sensitivity maps, each of the multiple initial images corresponding to a different set of the multiple sets of coil sensitivity maps;
    iteratively reconstructing, with a trained deep neural network, multiple images by using the multiple initial images and the multiple sets of coil sensitivity maps to generate multiple final images, each of the multiple images corresponding to a different set of the multiple sets of sensitivity maps; and
    combining the multiple final images output from the trained deep neural network to generate the MR image;
    wherein the multiple sets of coil sensitivity maps are estimated using an ESPIRiT calibration.

2. The method of claim 1, further comprising displaying the MR image via a display device.

3. The method of claim 1, wherein the trained deep neural network comprises a number of interleaved convolutional neural networks (CNNs) and data consistency layers.

4. The method of claim 3, wherein the trained deep neural network performs a number of iterations, each iteration performed by one CNN and a subsequent data consistency layer.

5. The method of claim 1, wherein the multiple initial images are zero-filled images.

6. A non-transitory computer-readable medium (CRM) comprising instructions that, when executed, cause a processor to:
    estimate multiple sets of coil sensitivity maps from undersampled k-space data, the undersampled k-space data acquired by a multi-coil radio frequency (RF) receiver array of a magnetic resonance (MR) imaging apparatus;
    reconstruct multiple initial images using the undersampled k-space data and the estimated multiple sets of coil sensitivity maps, each of the multiple initial images corresponding to a different set of the multiple sets of coil sensitivity maps;
    iteratively reconstruct, with a deep neural network, multiple final MR images by using the multiple initial images and the multiple sets of coil sensitivity maps as inputs to the deep neural network, each of the multiple final MR images corresponding to a different set of the multiple sets of sensitivity maps and output from the deep neural network; and
    combine the multiple final MR images output from the deep neural network to generate a combined, final MR image;
    wherein the deep neural network comprises a number of interleaved convolutional neural networks (CNNs) and data consistency layers.

7. The CRM of claim 6, wherein the deep neural network is trained end-to-end with artifact-free ground truth MR images and corresponding initial MR images reconstructed directly from undersampled MR data or augmented by simulated artifacts.

8. The CRM of claim 6, further comprising displaying the combined, final MR image to a user via a display device in electronic communication with the CRM.

9. The CRM of claim 6, wherein estimating the multiple sets of coil sensitivity maps includes estimating the multiple sets of coil sensitivity maps using an ESPIRiT calibration.

10. The CRM of claim 6, wherein each initial image of the multiple initial images is a zero-filled image.

11. The CRM of claim 6, wherein the deep neural network further comprises a residual connection placed in between couples of convolutions of the CNN.

12. The CRM of claim 6, wherein the deep neural network performs a number of iterations, each iteration performed by one CNN and a subsequent data consistency layer.

13. The CRM of claim 6, wherein the multiple initial images are complex-valued images and wherein the instructions further cause the processor to split the multiple complex-valued initial images into real part images and imaginary part images and input the split multiple complex-valued initial images into the CNN and input the multiple sets of coil sensitivity maps into the data consistency layers.

14. The CRM of claim 6, wherein the iteratively reconstructing includes iteratively reconstructing the multiple final MR images simultaneously with the deep neural network.

15. A magnetic resonance imaging (MRI) system, comprising:
- a radiofrequency (RF) coil array including a plurality of coil elements;
- a processor coupled to the RF coil array; and
- a non-transitory memory storing a deep learning-ESPIRiT network and executable instructions that when executed during operation of the MRI system cause the processor to:
  - acquire, with the RF coil array, undersampled k-space data;
  - estimate multiple sets of coil sensitivity maps from the acquired k-space data;
  - reconstruct a plurality of initial MR images using the acquired k-space data and the estimated multiple sets of coil sensitivity maps;
  - input the initial MR images and estimated multiple sets of coil sensitivity maps into the deep learning-ESPIRiT network and reconstruct a plurality of final MR images concurrently with the deep learning-ESPIRiT network; and
  - display one or more of the plurality of reconstructed final MR images.

16. The MRI system of claim 15, further comprising a display device in electronic communication with the processor and including a display screen and wherein the one or more of the plurality of reconstructed final MR images are displayed via the display screen.

17. The MRI system of claim 15, wherein each final MR image of the plurality of reconstructed final MR images corresponds to a different set of the multiple sets of coil sensitivity maps and wherein each set of coil sensitivity maps includes a sensitivity map for each coil element of the plurality of coil elements.

18. The MRI system of claim 15, wherein the deep learning-ESPIRiT network includes a deep neural network including a plurality of layers integrated with a data consistency layer and wherein reconstructing the plurality of final MR images concurrently with the deep learning-ESPIRiT network includes comparing and enforcing consistency between intermediate images generated from the deep neural network and the multiple sets of coil sensitivity maps.

* * * * *